US011576631B1

(12) United States Patent
Rubio et al.

(10) Patent No.: US 11,576,631 B1
(45) Date of Patent: Feb. 14, 2023

(54) SYSTEM AND METHOD FOR GENERATING A VIRTUAL MATHEMATICAL MODEL OF THE DENTAL (STOMATOGNATHIC) SYSTEM

(71) Applicant: Medlab Media Group, SL, Madrid (ES)

(72) Inventors: Marcos Rubio Rubio, Madrid (ES); Clara Soler Pellicer, Madrid (ES); Evgeny Solovykh, Moscow (RU); Alexander Obrubov, Moscow (RU); Svetlana Polyakova, Moscow (RU)

(73) Assignee: Medlab Media Group SL, Madrid (ES)

( * ) Notice: Subject to any disclaimer, the term of this patent is extended or adjusted under 35 U.S.C. 154(b) by 414 days.

(21) Appl. No.: 16/792,216

(22) Filed: Feb. 15, 2020

(51) Int. Cl.
| | | |
|---|---|---|
| *A61B 6/14* | (2006.01) | |
| *A61C 9/00* | (2006.01) | |
| *A61B 6/03* | (2006.01) | |
| *A61B 6/00* | (2006.01) | |
| *A61C 7/00* | (2006.01) | |

(Continued)

(52) U.S. Cl.
CPC ............ *A61B 6/14* (2013.01); *A61B 6/032* (2013.01); *A61B 6/4085* (2013.01); *A61B 6/466* (2013.01); *A61B 6/5217* (2013.01); *A61B 6/5294* (2013.01); *A61C 7/002* (2013.01); *A61C 9/0086* (2013.01); *G06T 7/0012* (2013.01); *G06T 17/00* (2013.01); *G06T 2207/30036* (2013.01)

(58) Field of Classification Search
CPC .................. G06T 7/0012; G06T 17/00; G06T 2207/30036; A61B 6/032; A61B 6/14; A61B 6/4085; A61B 6/466; A61B 6/5217; A61B 6/5294; A61C 7/002; A61C 9/0086

See application file for complete search history.

(56) References Cited

U.S. PATENT DOCUMENTS

| | | | | |
|---|---|---|---|---|
| 2014/0247260 | A1* | 9/2014 | Ghoneima | ............... G06T 19/00 345/419 |
| 2014/0294273 | A1* | 10/2014 | Jaisson | ................... A61C 7/002 382/131 |

(Continued)

OTHER PUBLICATIONS

Kato et al. "Three-dimensional imaging of internal tooth structures: applications in dental education." Journal of Oral Biosciences 58.3 (2016): 100-111. (Year: 2016).*

*Primary Examiner* — Katrina R Fujita
(74) *Attorney, Agent, or Firm* — Bardmesser Law Group

(57) ABSTRACT

A method for forming a virtual 3D mathematical model of a dental system, including receiving DICOM files representing the dental system; identifying number and location of voxels of tissues of the dental system; combining the voxels of the tissues into voxels of organs of the dental system; combining the organs into the virtual 3D mathematical model of the dental system, wherein the virtual 3D mathematical models supports linear, non-linear and volumetric measurements of the dental system; and presenting the virtual 3D mathematical model to a user. The DICOM files can be cone beam or multispiral computed tomography, MRT, PET and/or ultrasonography. The tissues include enamel, dentin, pulp, cartilage, periodontium, and/or jaw bone. The organs include teeth, gums, temporomandibular joint and/or jaw. A size of the voxels is typically between 40 μm and 200 μm.

14 Claims, 13 Drawing Sheets
(6 of 13 Drawing Sheet(s) Filed in Color)

(51) Int. Cl.
*G06T 17/00* (2006.01)
*G06T 7/00* (2017.01)

(56) References Cited

U.S. PATENT DOCUMENTS

| | | | | |
|---|---|---|---|---|
| 2014/0329194 | A1* | 11/2014 | Sachdeva | A61C 7/002 |
| | | | | 433/24 |
| 2016/0045282 | A1* | 2/2016 | Levin | A61C 9/0053 |
| | | | | 700/98 |
| 2016/0135925 | A1* | 5/2016 | Mason | A61C 7/002 |
| | | | | 703/2 |
| 2018/0078347 | A1* | 3/2018 | Falkel | A61B 1/000094 |
| 2019/0231492 | A1* | 8/2019 | Sabina | A61B 1/000096 |
| 2019/0269485 | A1* | 9/2019 | Elbaz | A61B 1/24 |
| 2020/0364624 | A1* | 11/2020 | Kearney | G16H 50/20 |
| 2020/0387829 | A1* | 12/2020 | Kearney | G06T 5/002 |
| 2021/0209764 | A1* | 7/2021 | Gohs | G06T 7/194 |

* cited by examiner

SYSTEM AND METHOD FOR GENERATING A VIRTUAL MATHEMATICAL MODEL OF THE DENTAL (STOMATOGNATHIC) SYSTEM

The patent or application file contains at least one drawing executed in color. Copies of this patent or patent application publication with color drawing(s) will be provided by the Office upon request and payment of the necessary fee.

BACKGROUND OF THE INVENTION

Technical Field

The claimed invention relates to dentistry (all branches), anatomy, and X-ray studies, and, more particularly, to 3D mathematical modelling of the dental system.

Background of the Related Art

X-ray diagnostics is a supplementary method used by dentists. X-ray diagnostics is non-invasive and allows to examine human and/or animal tissues using radiocontrast agents. The main drawback of X-ray diagnostics is that 2D images provide much displacement caused by overlapping tissues. Cone beam computed tomography (CBCT) [6, 7, 8, 11, 12, 13] allowed to significantly improve image accuracy in order to examine organs and tissues in various sections, such as coronal plane, sagittal plane, and transversal plane, wherein tissues seem to be rendered in 3D. However, the resulting image is a 2D still made in three planes, i.e., no actual anatomical 3D image of tissues and organs is produced (see FIGS. 1-6). A 3D image is generated by means of 3D rendering [see 6, 9, 10, 14, 15, 18, 19, 20, 21, 22]. The resulting model suffers from significant losses caused by the specifics of the procedure. Also, this process does not support mathematical modelling of the functional clinical situation of the dental system and changes therein.

CBCT has enabled dentists to take linear measurements, such as root canal length. Points of measurement, however, are selected by the dentist, which may be a source of errors, too. Also, CT scans are assessed by the dentist or radiologist, which makes the process prone to subjectivity. Besides, a human is incapable of measuring and assessing volumetric dimensions of anatomical masses and pathologies, unaided. A mathematical model would allow to automatically, using computer-based analysis, take objective linear and volumetric measurements of elements and organs of the dental system, store and compare them, model possible treatments or surgeries, and predict their outcomes.

Today, dentists use jaw models made of gypsum (analog models) and virtual jaw models generated by scanning gypsum models or the patient's oral cavity. Regardless of the source, virtual solid models (.stl-file) allow to see the surface images of teeth and gums. Such models have the same drawbacks as CT scans. Moreover, they can't show the state of tissues, pulp, roots and root canals, restorations, etc.

SUMMARY OF THE INVENTION

A virtual mathematical dental model is created based on further analysis of a CT scan, which makes it possible to generate a complete individual anatomical virtual dental image with linear, angular, and volumetric parameters of the dental system as a whole, as well as of its elements, which allows to objectify clinical features of the dental system.

In one aspect, there is provided a method for forming a virtual 3D mathematical model of a dental system, the method including receiving DICOM files representing the dental system; identifying number and location of voxels of tissues of the dental system; combining the voxels of the tissues into voxels of organs of the dental system; combining the organs into the virtual 3D mathematical model of the dental system, wherein the virtual 3D mathematical models supports linear, non-linear and volumetric measurements of the dental system; and presenting the virtual 3D mathematical model to a user.

The process of combining the voxels of the tissues into voxels of organs of the dental system, and the generation of the final 3D model of the dental system is automated, and relies on artificial intelligence (AI) as one option. The AI is based on image recognition algorithm(s), combined with deep learning algorithms, which together are used to form a neural network that is capable of being trained. The AI identifies the contrast of the tissues, and combines them into organs based on the intensity of the voxels' grey scale, and then combines the organs into the dental system, creating a coordinate system and reference points for mathematical analysis. The use of one or several neural networks for this task makes sense, since the input is a set of voxels with specific mathematical characteristics (location, size and grey scale), which in turn permits a neural network to efficiently process the information and identify dental tissues and artificial objects. Deep learning algorithms based on the use of multiply-used examples of the identified objects (tissues, organs, the entire dental system). Once the training is completed, an application can use the neural network to quickly and efficiently identify the tissues and organs of the dental system of a specific patient. The data can then be converted to image format for display to the user.

The DICOM files can be based on any of cone beam or multispiral computed tomography, MRT, PET and ultrasonography. The tissues include enamel, dentin, pulp, cartilage, periodontium, and jaw bone. The organs include teeth, gums, temporomandibular joint and jaw. A size of the voxels is typically between 40 μm and 200 μm, although improved scan resolution in the future will permit even smaller voxels. Optionally, the virtual 3D mathematical model includes any of presence or absence of teeth, shape of the teeth, number of roots in the teeth, root canals in the teeth, pulp stones in the teeth, nodular masses in the pulp of the teeth, calcified masses in the pulp of the teeth, dental fillings, restorative objects, dentures, dental posts, parapulpal pins, dental filling materials, quality of root canal fillings, dental bone implants, and prosthetic dentures supported by implants. Optionally, the virtual 3D mathematical model includes any of linear dimensions of teeth and parts of teeth in sagittal, frontal, and transversal planes, length of root canals, shapes and diameters of the root canals, areas of occlusal surface and contacts, areas of points of contact, volumetric dimensions of defects in hard tissues of teeth and jawbones, and volumetric dimensions of restorations.

Optionally, the virtual 3D mathematical model compares an initial state of the dental system to a later state of the dental system. Optionally, the virtual 3D mathematical model shows dynamical aging of the dental system over time. Optionally, the virtual 3D mathematical model calculates biomechanics of individual elements of the dental system or the system as a whole. As example, by knowing the length and thickness of the root, and given the material properties of the dentin (density, composition, strength, etc.), it is possible to calculate the biomechanical characteristics of the root, and to then suggest a structure for restoration of the root and the tooth, such as inserts and crowns.

Optionally, the virtual 3D mathematical model's temporomandibular joint movement data using axiography to replicate a virtual natural movement of a lower jaw. Optionally, the virtual 3D mathematical model allows to plan, monitor and predict the outcome of dental treatment and surgery with regard to the individual characteristics of the patient. Optionally, the virtual 3D mathematical model sets up a coordinate grid used to calculate location and volumetric parameters of dental treatment. Optionally, the virtual 3D mathematical model combines with scanning dental system, 3D printing and CAD/CAM technologies.

Additional features and advantages of the invention will be set forth in the description that follows, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE ATTACHED DRAWINGS

The patent or application file contains at least one drawing executed in color. Copies of this patent or patent application publication with color drawing(s) will be provided by the Office upon request and payment of the necessary fee.

The accompanying drawings, which are included to provide a further understanding of the invention and are incorporated in and constitute a part of this specification, illustrate embodiments of the invention and together with the description serve to explain the principles of the invention.

DETAILED DESCRIPTION OF EMBODIMENTS OF THE INVENTION

Reference will now be made in detail to the preferred embodiments of the present invention, examples of which are illustrated in the accompanying drawings.

The claimed invention is presented in the following embodiment: a CBCT scan is taken to provide a 3D image of the dental system. The detailed description of the equipment and methodology used in CT, as well as of technical features of the CT scan is provided in [6]. The present invention involves a further analysis of the CT scan of the dental system in order to generate a virtual mathematical model.

The CT scan of the dental system is stored in the DICOM format, an international standard for medical images [1, 2, 3, 4, 5, 6, 17]. Each such image is made up of voxels with sizes ranging from 40 μm to 200 μm. (It is expected that with improvements in imaging technology, the voxel size will become smaller, down to micron-sized voxels.) Each voxel contains information about image accuracy depending on the sizes and densities of tissues using up to 65,524 shades of gray [6].

Figure 9:
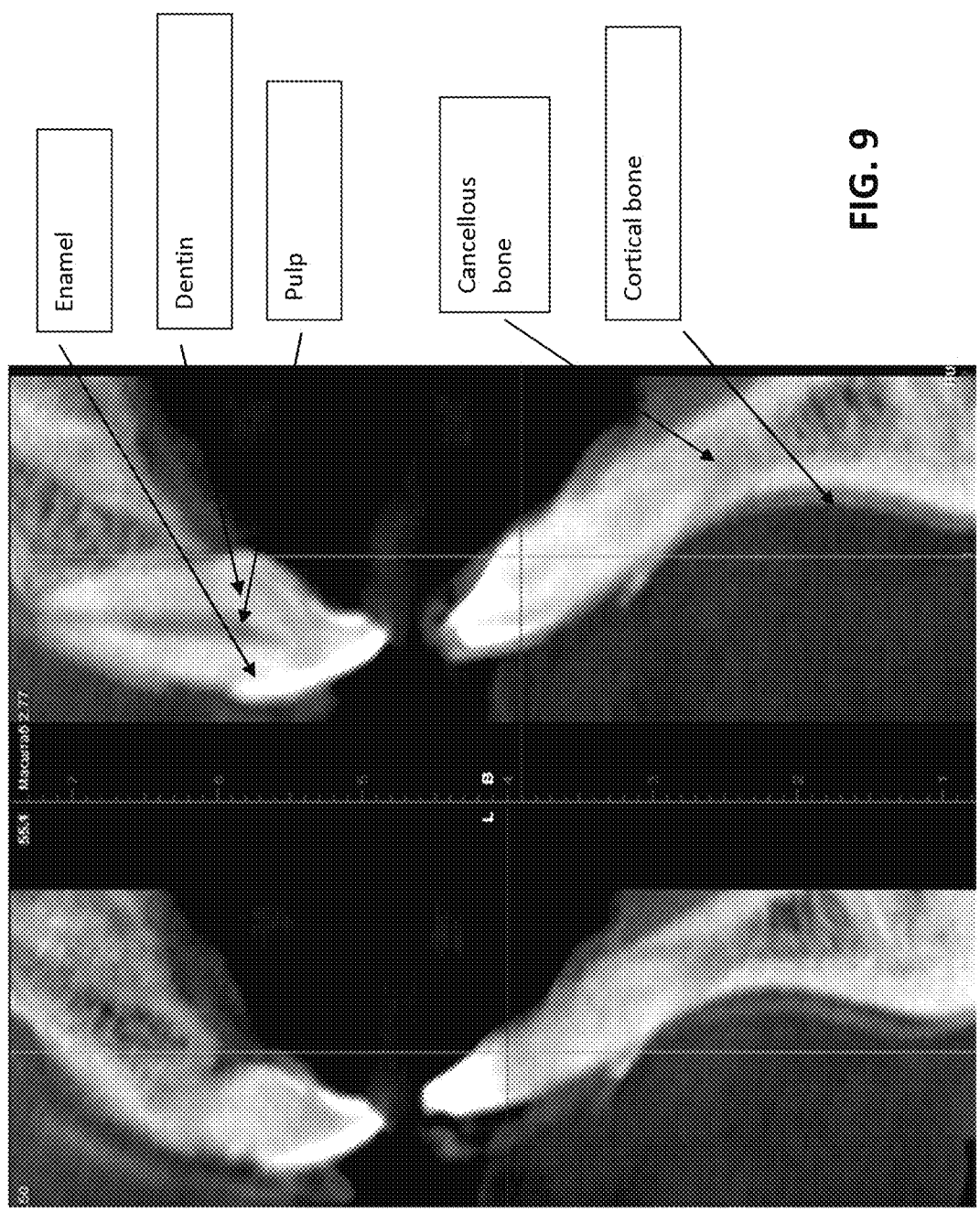
FIG. 9 shows locations of tooth and jaw tissues on the sagittal section of a CT scan.
Figure 10:
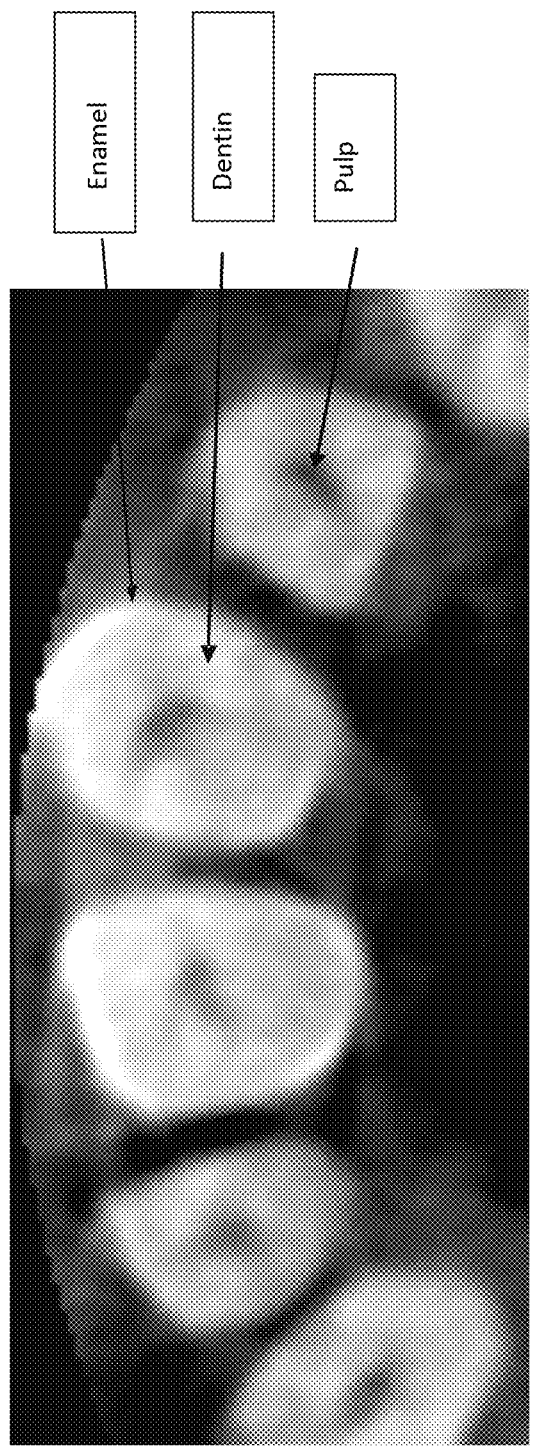
FIG. 10 shows locations of tooth and jaw tissues on the coronal section of a CT scan.

The algorithm for generating a virtual anatomical model is as follows (see FIG. 11):

1. Voxels with similar characteristics are joined into groups corresponding to some biological tissue, organ, or system, which are presented as layers in all planes. In FIGS. 9 and 10, for instance, enamel, dentin, bone, pulp, periodontium, and elements of the temporomandibular joint are shown.

2. Tooth tissues are joined into a model of a tooth. This step is repeated for each tooth, thus providing virtual models for all teeth. In this step, tooth restorations and traces of root canal treatment can be detected.

3. Virtual models of the upper jaw and the lower jaw, as well as of periodontium and the elements of the temporomandibular joint are created.

4. Finally, all virtual models are combined into a single virtual model of the entire dental system.

The DICOM format contains the image of the object under examination, that is broken into layers in the sagittal, axial (transversal, or horizontal), and frontal planes according to voxel sizes. Layer by layer, the parts of the image are joined across all planes, resulting in a single 3D image showing all tissues, organs and elements of the dental system. The elements of the dental system (teeth, bones, temporomandibular joints) are recognized using computed analysis. Voxels, being minimum units of measurement, allow the computer to examine both qualitative and quantitative (i.e., linear, angular, and volumetric) parameters of individual virtual models for each object, e.g., a tooth (tooth crown dimensions, root canal length, extent of solid tooth or bone tissue decay, the area of the tooth root inside the bone, etc.).

FIG. 9 shows locations of tooth and jaw tissues on the sagittal section of a CT scan. FIG. 10 shows locations of tooth and jaw tissues on the coronal section of a CT scan. FIGS. 9 and 10 illustrate shape and construction of hard tissues, restorations of teeth and bone tissues in sagittal and coronal section (traditional CBCT (cone bean computer tomography) picture). Based on section positioning, the hard and soft tissues can be studied at different points in sagittal and coronal plane. However, none of figures, not even all sections in both planes, give an opportunity to understand volumetric (3D) shape (make accurate shape and size) and relationship all tissues to each other. Today, on the other hand, there is an opportunity to do linear measurement of tissue and organs (teeth, root canal, defects, restorations and others), but all structures and defects are volumetric, which means that a mathematical model of the dental system will allow to do volumetric shapes of interest area, tissues and defects, they relationships and will do volumetric measurements.

By having a unit of measurement, it is possible to obtain coordinates of all elements of the dental system in order to provide mapping tools for the dentist or robot. For instance, the present invention allows to calculate the extent of solid tooth tissue destruction and proximity of defects to the pulp, which is an important and objective criterion for deciding on whether it is possible to save the pulp. In case of periodontal diseases, it is also possible to assess the extent of bone tissue destruction in order to better assess the strength reserves of the remaining periodontium.

The proposed model allows to obtain linear, angular, and volumetric parameters of the tooth root canal system (see FIG. 12), which makes endodontic treatment more predictable and accurate by calculating the projection of a root canal on the chewing, palatial, or lingual surface of the tooth (pulp trepanation spot), as well as of the canal length, curvature, and volume (shape) at the diagnostics stage, before the actual surgery.

Volumetric and linear dimensions of tooth crowns and roots allow to accurately plan, model, and monitor the outcome of the dental surgery.

When all elements of the dental system have been combined into a single virtual model, it results in a complex virtual anatomical model of the entire dental system of a particular patient and/or animal. This would allow to preserve qualitative and quantitative parameters of all elements of the dental system, thus providing individual qualitative and quantitative (i.e., linear, angular, and volumetric) parameters of the entire dental system, when the elements have been combined, which paves the way to a fundamentally new and personalized approach to dental treatment, taking into account all individual characteristics of the patient's dental system.

The virtual anatomical model of the patient's dental system can be used as a reference point that reflects the structural and functional situation of the dental system at a particular moment in time. This would allow calculating mathematical parameters of the dental system (linear, angular, and volumetric dimensions of individual teeth, sizes of all teeth, jaw sizes, tooth locations in the jaws, correlations between upper and lower teeth and jaws, or between the elements of the temporomandibular joint) again and again for each new state. The combination of these parameters provides a fingerprint of sorts that can be used to identify a patient and/or animal.

Radiographic characteristics of voxels change depending on the image intensity. The higher the density of a tissue is, the higher the voxel intensity, i.e., voxels become whiter. Thus, tissues with varying densities are represented by voxels of different intensity. Tissue density, in turn, depends on its biochemical composition, particularly, the amount of minerals in it. Biochemical composition of tissues (bone, enamel, dentin) determines their strength and biomechanical properties. Taken in combination with absolute mathematical parameters of the elements of the dental system and the system as a whole, these properties allow to obtain individual strength (biomechanical property) values for each element and the system as a whole, which can then be used in clinical practice for individual calculations of tooth preparation and restoration parameters. Correlations between radiologic intensity of solid tissues in the dental system is an important diagnostic feature that allows to determine their biochemical composition in a non-invasive way.

The initial state of the dental system can be used as a reference point for modelling and planning the outcome of the proposed treatment, for comparing initial parameters with those obtained, and for objectively and dynamically monitoring aging changes in the dental system.

By combining the virtual anatomical model of the dental system with its functional data (electromyography of chewing muscles, Doppler ultrasound of vessels, axiography of the temporomandibular joint, stabilometry, etc.) it becomes possible to model the movement of the lower jaw in real time and taking into account individual degrees of freedom, which allows to monitor, model, and control the changes in the functional situation of the dental system that may be caused by the pathology affecting it or treatment. Besides, it is possible to draw connections between the changes in the functional situation of the dental system and changes in other systems of the body (postural system, cardiovascular system, nervous system, etc.).

Such mathematical models can be generated for bones and joints, muscles, as well as for any other system of a human and/or animal body.

Figure 1:
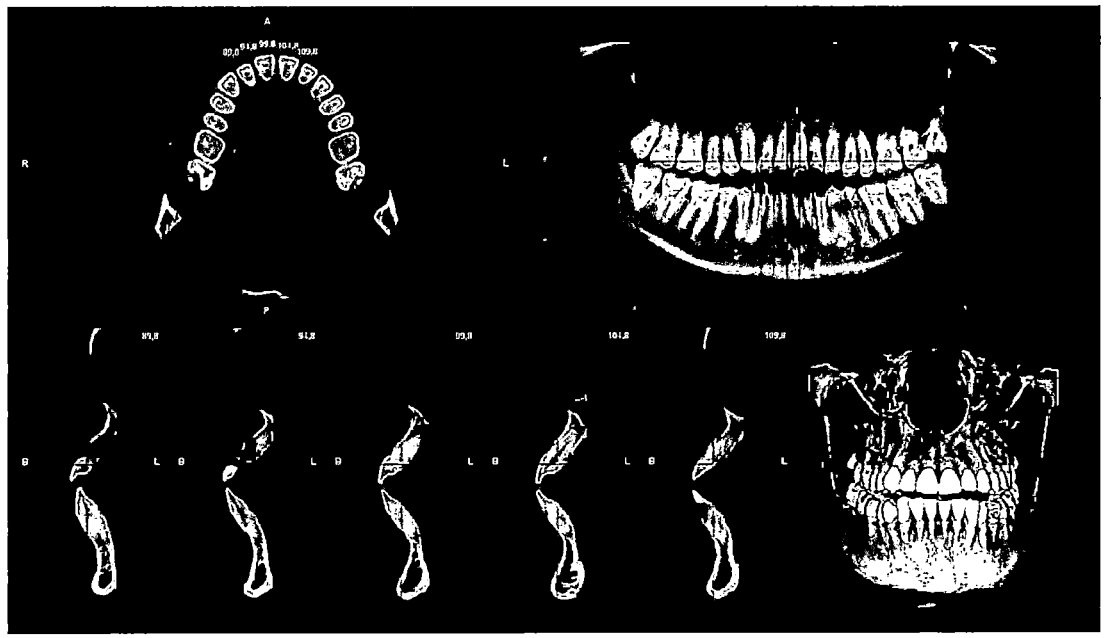
FIG. 1 shows a general overview of a cone beam computed tomography (CBCT) scan of the dental system.

FIG. 1 shows a general overview of a cone beam computed tomography (CBCT) scan of the dental system. FIG. 1 illustrates the interface of PLANMECA (the dental CBCT application used by dental practitioners), which is a common view of dental CBCT.

Figure 2:
FIG. 2 shows a transversal (horizontal) section of the teeth in the lower jaw on the tooth neck level of the teeth Nos. 18, 17 in the Universal Numbering System), with linear measurements provided.
Figure 3:
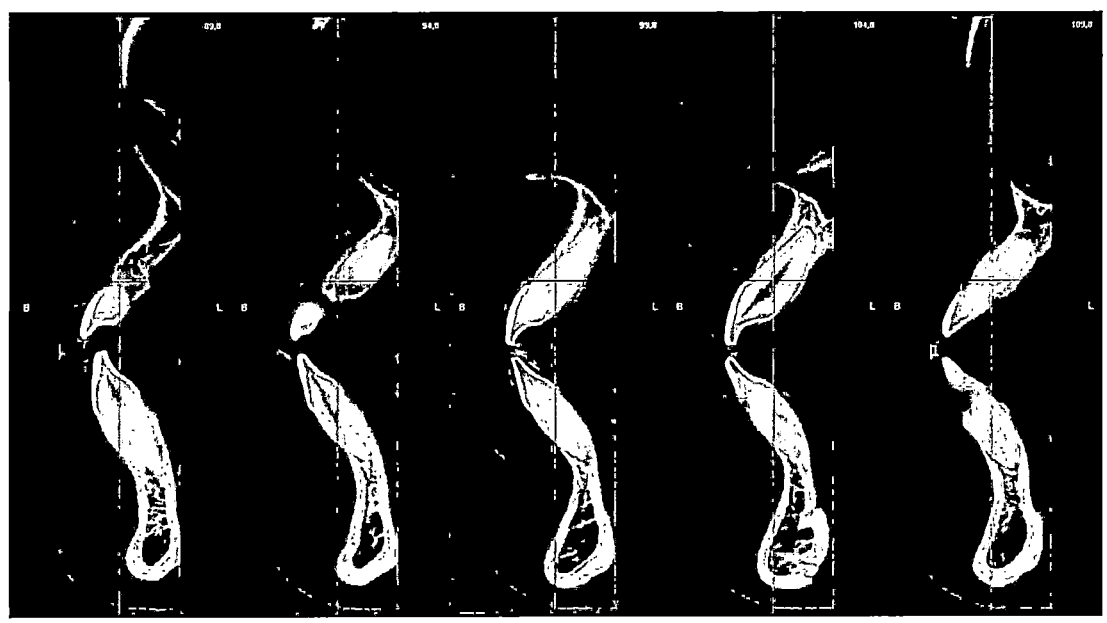
FIG. 3 shows a sagittal section on the level of the teeth Nos. 8, 9, 10, 11, 12 (Universal Numbering System).
Figure 4:
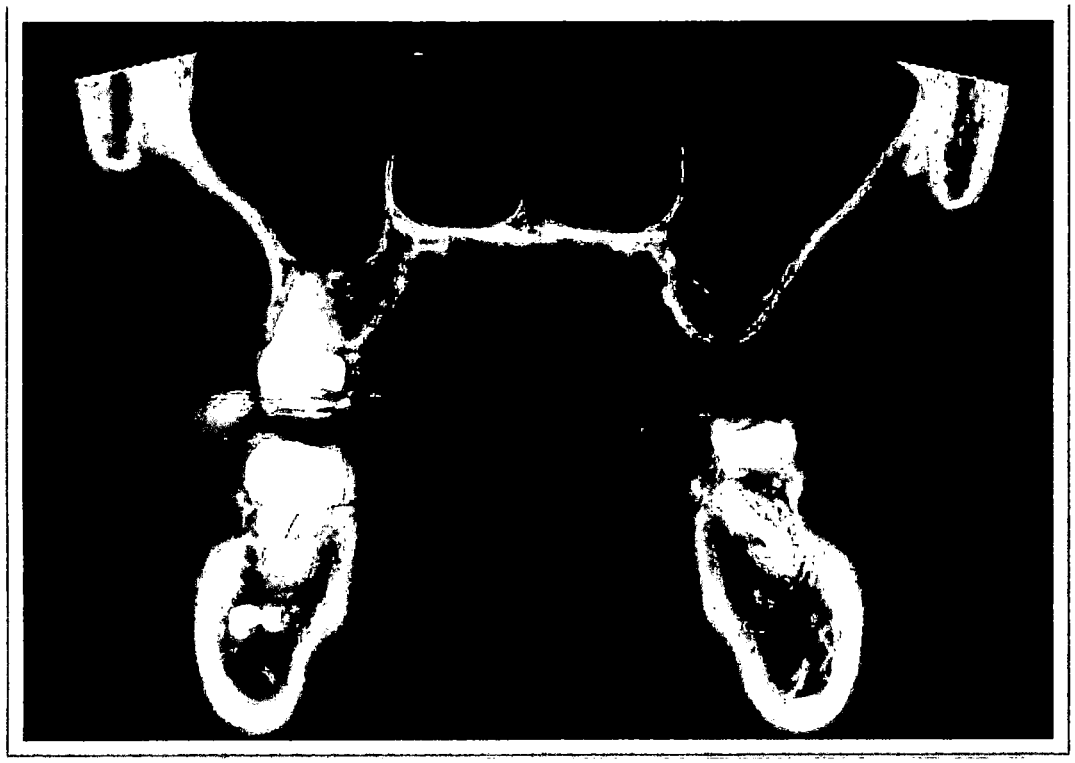
FIG. 4 shows a frontal section on the level of the teeth Nos. 4, 13, 20, 29 (Universal Numbering System).
Figure 5:
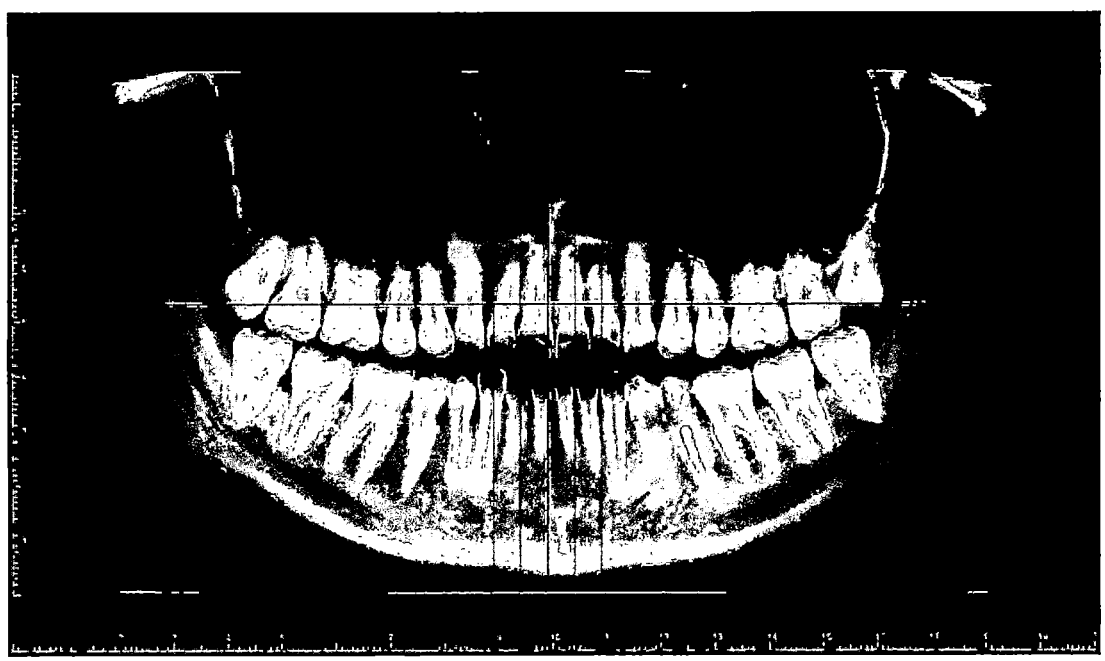
FIG. 5 shows a general overview of the dental system (orthopantomogram).

FIG. 2 shows a transversal (horizontal) section of the teeth in the lower jaw on the tooth neck level of the teeth Nos. 18, 17 in the Universal Numbering System), with linear measurements provided. FIG. 3 shows a sagittal section on the level of the teeth Nos. 8, 9, 10, 11, 12 (Universal Numbering System). FIG. 4 shows a frontal section on the level of the teeth Nos. 4, 13, 20, 29 (Universal Numbering System). FIG. 5 shows a general overview of the dental system (orthopantomogram). Generally, FIGS. 1-5 illustrate all structures of the dental system in sagittal, transversal and frontal planes. These images are presented as 3D objects, although, in reality, they are 2D pictures of sections of the dental system in different planes. Based on these images, it is theoretically possible to create a 3D image of each tooth, the jaw, and the entire dental system (such as shown in FIG. 6, discussed below), while it is not possible to do volumetric measurements, and even linear measurements are difficult and sometimes impossible to do.

Figure 6:
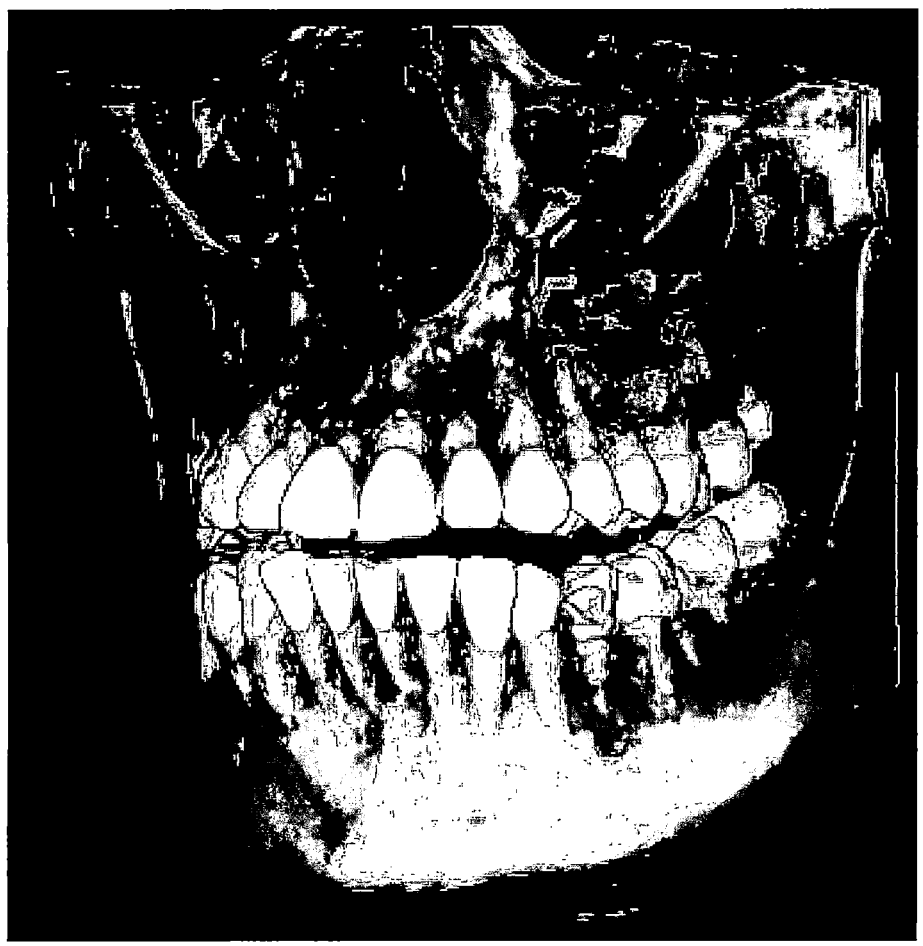
FIG. 6 shows a virtual model of both the upper and lower jaws generated based on the CT scan.

FIG. 6 shows a virtual model of both the upper and lower jaws generated based on the CT scan. This is a PLANMECA rendering of a CBCT picture. The 3D model of the dental system includes hard tissues of the dental system that can be used as a demonstration model, however, this model is quite inaccurate, does not fully show all the tissues, and it is difficult to make measurements. The "3D" images are not actually 3D—they are merely a set of cross-sections combined into a visual simulation of 3D, but not a real 3D model.

Figure 7:
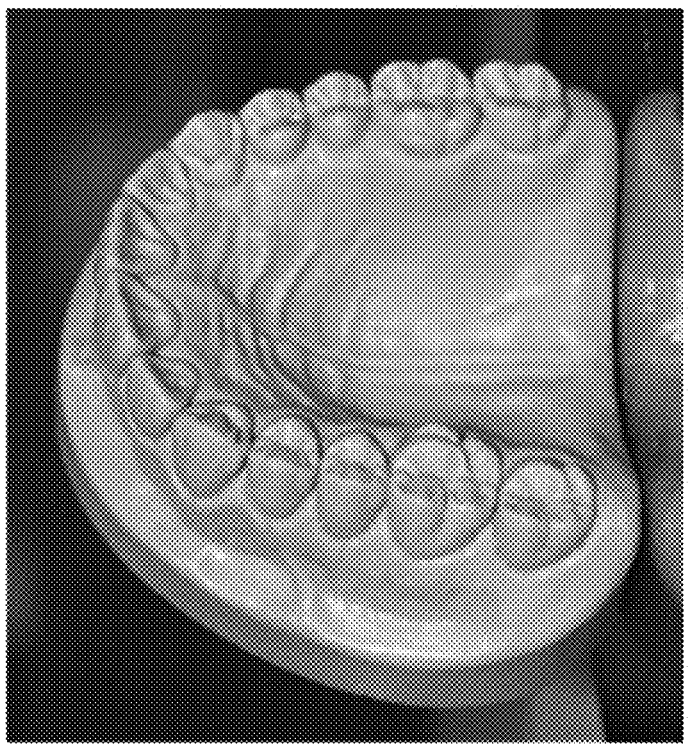
FIG. 7 shows an upper jaw model made of gypsum.
Figure 7:
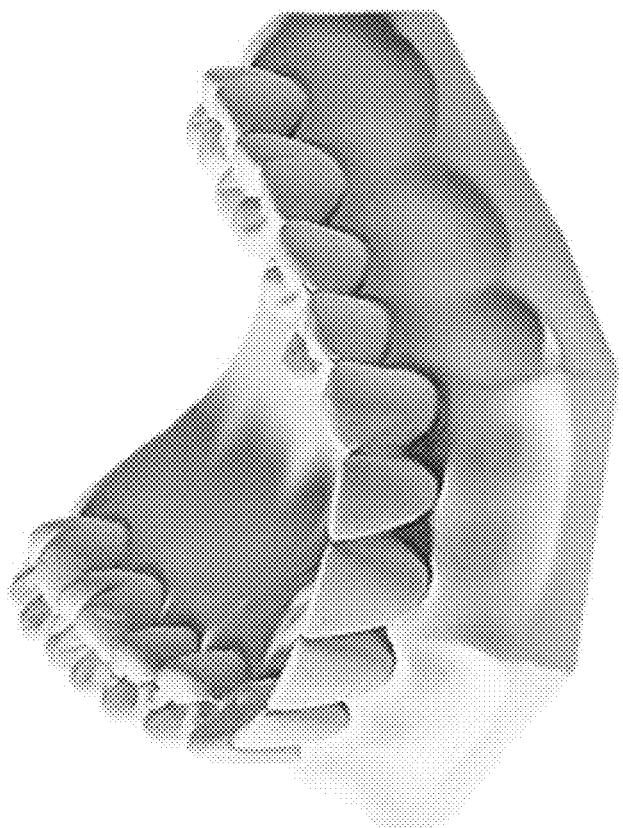

FIG. 7 shows an upper jaw model made of gypsum. One of the models often used in dentistry is the gypsum model, which is a type of solid models that can demonstrate the surface of gingiva, dental crown and part of the root. Its disadvantages, however, include the fact that not all the tissues of the dental system are present, surface structure can only be estimated, and any measurements are linear (not volumetric).

Figure 8:
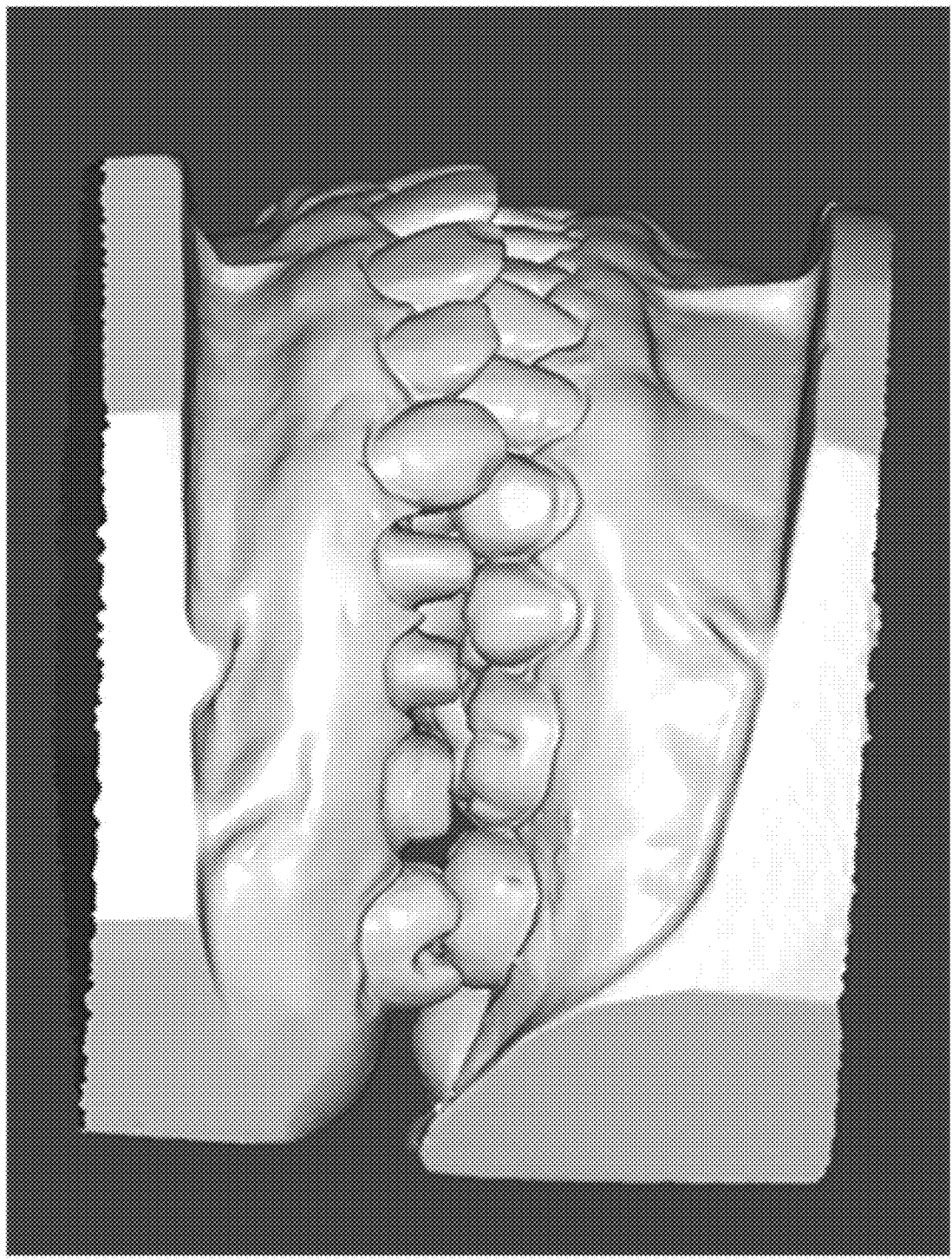
FIG. 8 shows virtual models of the upper jaw and lower jaw.

FIG. 8 shows virtual models of the upper jaw and lower jaw. This is an example of another model used in dentistry, particularly in CAD/CAM technology. This virtual solid model shows surface of gingiva, a dental crown and parts of the root virtually. However, this approach has the same problems—not all tissues are present, surface structures can only be estimated, and only linear distances measured.

Figure 11:
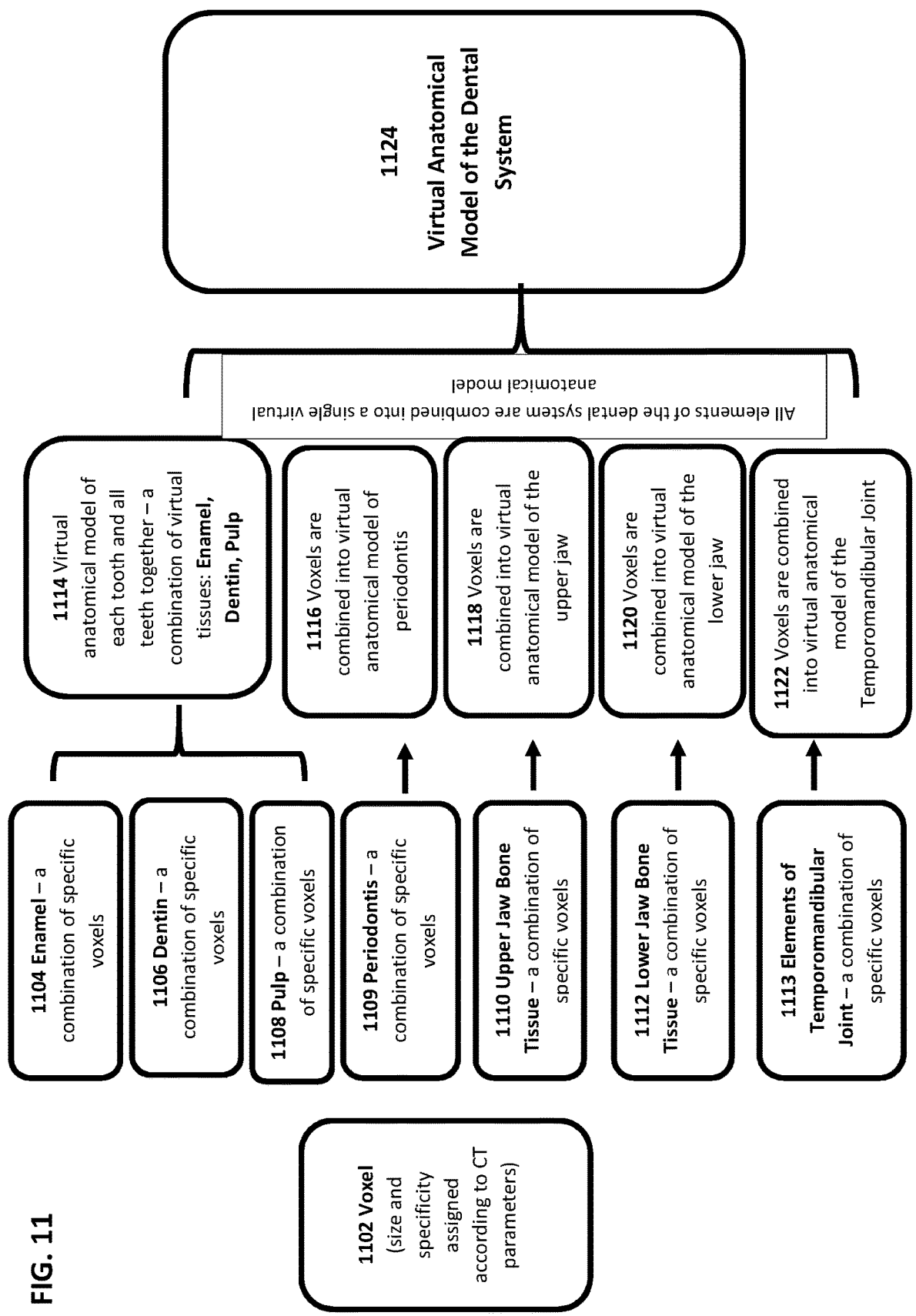
FIG. 11 shows a flowchart of generating a virtual mathematical model of the dental system.

FIG. 11 shows a flowchart of generating a virtual mathematical model of the dental system. The process starts with step 1102, where the generation of the CBCT (Cone Bean Computer Tomography) image (in DICOM format) occurs using a sensitive matrix of a tomograph by X-ray. This process is the coding each tissue in a voxel. Depending on the structure, density and biochemical composition voxel has its number of the grey scale. The tissues with high density have a low intensity in gray scale (since high density objects, such as metal fillings, are less transparent to X-rays), and low density tissue has a high intensity in grey scale.

Also, each tomograph adjusts the size of the voxel form 40 μm to 200 μm, depending on the resolution of the CBCT equipment, which results in more or fewer sectionals (in other words, the sections are performed every 40 μm to 200 μm, depending on the CBCT equipment resolution). Thus, each voxel (unit) has size and grey scales information, and the final CBCT image is a set of voxels—and each voxel has size information and grey scale.

Then, in step 1104, the voxels are combined based specific grey scale, to represent specific tissues—this is the way or process of tissue recognition. This is done using software filters. The filter selects the voxels with the same grey scale value. Of the natural tissues, enamel has the highest density and the lowest grey scale value in tomographic images, being the densest, most mineral rich and most homogeneous tissue. Thus, the voxels with the lowest value of the grey scale represents the enamel A mathematical calculation is performed to define the number, location and sequence of the voxels. Once the unit of calculation is defined—the voxel with the given size—and knowing their location, it is now possible to calculate the shape, linear dimensions and general volume of the enamel, and to map its coordinates. This results in a digital model of the enamel as a modeling object. This procedure is repeated for all teeth, and the model will represent the enamel of all the teeth. This process is possible because the combination of the similar voxels in an anatomical or artificial structure is recognized by a computer. Based on size of voxel (which is the unit of measurement), the computer creates estimates linear and volumetric measurements of each tissues with high accuracy.

Today, a number of enhancement methods for CBCT images exist. In principle, the various shades of gray that make up the display are determined by the density of a structure and the amount of X-ray energy that passes through it. This phenomenon is referred to as attenuation. In conventional CT imaging, the relative amount of radiation attenuated by each voxel element is represented by the CT number, defined as the difference in attenuation of the contents of the voxel relative to water. CT number=[μstructure−μwater]F, where: μstructure=attenuation of the structure, μwater=attenuation of water, and F=a scaling factor used to define the scale of numbers over the range of values encountered in the body. This scale is commonly referred to as the Hounsfield scale and expressed in Hounsfield Units (HU). In the Hounsfield scale, water is given a value of zero and air a value of −1000. The numeric value of the scale is dependent on the recording and display capabilities of the CT scanner. For example, a CT with a 12-bit detector is capable of recording grayscale differences of 212 (4096 shades of gray). This corresponds to a CT number scale from −1000 for air (e.g., the oropharynx) to +3095 for the densest object that can be measured by the scanner (e.g., compact bone). However, while a 12-bit device is able to measure tissue attenuation within a range of 4096 CT numbers, the human eye is not capable of distinguishing this range of pixel intensities. Nor are most monitors used in dentistry capable of displaying more than 256 levels of gray. Therefore, the available grayscale must be mapped onto the portion of the Hounsfield scale that is to be displayed. This mapping is performed by adjusting two parameters, the window level and window width. The window level specifies the CT number for centering the grayscale whereas the window width defines the range of CT numbers over which the grayscale is to extend.

Image Filters are secondary image enhancement tools used to improve image quality and diagnostic interpretability. The most common filtering operations are smoothing and sharpening. They act on an image matrix kernel through the application of various convolutions. Smoothing filters remove random inhomogeneities that provide the speckled appearance of the image. Most often, such random inhomogeneities are originated by noise, including in particular quantum radiographic noise. In maxillofacial imaging, this filter is most advantageous with thin sections, where image noise results in a "salt and pepper" appearance within the image. Sharpening filters either enhance the detection of edges or emphasize existing edges of objects and adjust the contrast and the shade characteristics of the image. While most operate in the spatial domain (unsharp masking, Sorbel (3×3 matrix) or Laplacian (5×5 matrix)) by the application of kernels, others can be applied in the frequency domain (Fast Fourier Transform). Most are applied to images that have good contrast (an appropriate level of darkness and lightness) but blurry edges. This involves rotation of the volumetric dataset in three orthogonal dimensions to coincide with specific topographic reference planes so that sectional images present bilateral anatomic structures accurately without parallax misrepresentation. When CBCT images are represented on a display monitor at an image matrix/display matrix ratio of 1:1, they may be too small for adequate visual interpretation in which case CBCT images are displayed on monitors as magnified images. Excessively zoomed images have a blocky appearance (pixilation), reflecting the larger size of each effective pixel. Although the application of a smoothing filter can reduce this pixelation effect, a more visually pleasing result can be generated using spatial interpolation techniques. (see [23], Scarfe & Angelopoulos, 2018)

In step 1106, the formation of the voxels representing the dentin of a single tooth is performed in a similar manner as in step 1104. This results in a mathematical digital model of a single tooth's dentin. This process is then repeated for all the teeth, and the model will represent the dentin of all the teeth.

Using the same algorithm as above, the mathematical models for the tissues of the pulp, periodontium, the upper jaw bone tissue, the lower jaw bone tissue, and the temporomandibular joint, are created, see steps 1108, 1109, 1110, 1112, 1113.

Then, in step 1114, based on the principles of anatomical construction, the elements (at this point, tissues) are joined into mathematical models of the organs (e.g., dentin, enamel, pulp), the jaw and the temporomandibular joint. At this stage, the software creates the mathematical model of the organ (here, the tooth) from the models of the enamel, pulp and dentin that comprise that particular tooth, and identifies this organ (i.e., that this organ is a tooth, and which tooth it is, or that this organ is a lower jaw, or upper jaw, etc.).

Creation of the virtual model of the teeth is performed as follows: The model of the enamel of each tooth has a shape of a cap, which is congruent with the model of the dentin, which permits comparing and matching the two models, and other tissues. A DICOM image has voxels, some of which encode information about the inner layer of enamel and the outer layer of dentin—these intermediate voxels serve as "bridges", and are the comparison points for matching the electronic models of the enamel and the dentin for each tooth. Given that the virtual tissues are represented as mathematical models using voxels as units, further combination of the tissues into an organ (e.g., a tooth) permits creating the model of the entire tooth. Thus, the mathematical model of the organ permits calculating linear and volumetric parameters of the organ and its tissues, their relative position to each other, the presence of any defects and structural peculiarities, and to superimpose a coordinate system onto the organ.

Based on the above, the mathematical models of the periodontium, the upper jaw bone tissue, the lower jaw bone tissue, and the temporomandibular joint, are created in the same manner, see steps 1116, 1118, 1120, 1122, respectively.

The next step 1124 performs the joining of all the virtual elements (now, organs) of the dental system into a single virtual model of the dental system. The mechanism of the joining relies on the congruency principle—for a single root of a tooth, there is one alveolus in the jaw that matches it. At the voxel level, there is a dual formation of the "bridges"—voxels that carry information about the dentin and the periodontium permit comparing the models of the dentin and the periodontium, while the voxels that carry information about the periodontium and the bone tissue of the alveola permit comparing the models of the periodontium and the jawbone. Thus, the virtual models of the teeth and the jawbone are joined into a single model. The other models are joined together in a similar manner. The result is a virtual mathematical model of the entire dental system, which visualizes the structure of all the organs and the tissue, which permits a detailed high-quality analysis of the structural and clinical aspects of the elements and the tissues of the dental system. The model also permits all types of measurements, such as length, width, and volume of the root canal, the volume of the cariotic defect (decay) and the distance to the pulp of the tooth, as well parameters of the entire dental system (the shape and dimensions of the arch and how well it matches the tooth size, for example). It also permits more complex measurements involving nonlinear algebra (i.e., involving lines and distances that are not direct point-to-point, but involve curved lines and surfaces), and developing a coordinate system for the entire dental system.

Conventionally, practitioners can estimate tissue and structures based on their subjective assessment (256 colors of grey scales), they cannot produce a 3D model from 2D slices, and only linear measurements are possible. The proposed approach permits treating all elements of the dental system separately and then together, using both linear and nonlinear mathematical analysis. The model permits analysis of the current state of the dental system, as well as the evolution of the dental system over time (such as physical growth and aging of the patient, any dental work performed, and so on. This permits to better control the process of tooth and jaw development. It also permits better prognosis of any dental and orthodontic pathologies. The virtual model permits much more precise individual patient diagnostics and better patient-specific treatment. Thanks to precise linear and volumetric measurements of all the elements of the dental system, it is possible to non-invasively identify the parameters of the defects and decay, distances of the defects in the tooth tissue to the pulpal chamber, measure the bone defects, the shape and length of the pulpal chamber, and to calculate its volume. Another advantage is that the model permits a mathematical assessment of any proposed tooth restoration, while any human factor in the assessment is minimized.

Figure 12:
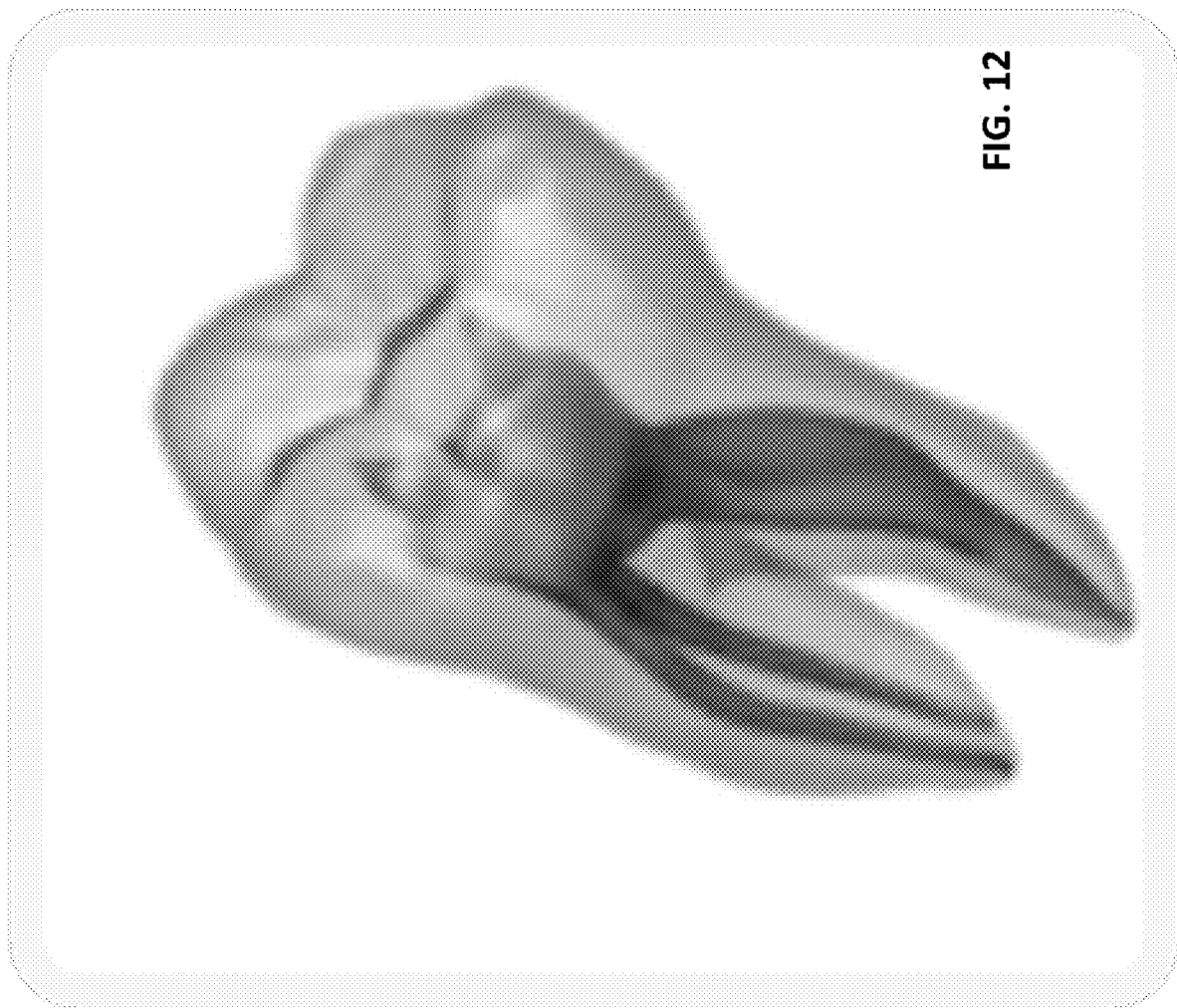
FIG. 12 shows a diagram of a virtual mathematical model of a tooth, in which the root canal system is rendered.

FIG. 12 shows a diagram of a virtual mathematical model of the tooth. This model visualizes hard and soft dental tissues. Each tissue has specific transparent color, and the virtual mathematical model is movable and rotatable, allowing the dentist to observe the tooth from a number of different angles. The model also permits observing relationships between tissues, artificial and anatomical structures, and also permits to highlighting specific tissues and areas, and to generate linear and volumetric parameters (for example, the pulp chamber, the root canal, its shape, length, width, curve, proximity to defects). The practitioner can see detail from different angles.

Figure 13:
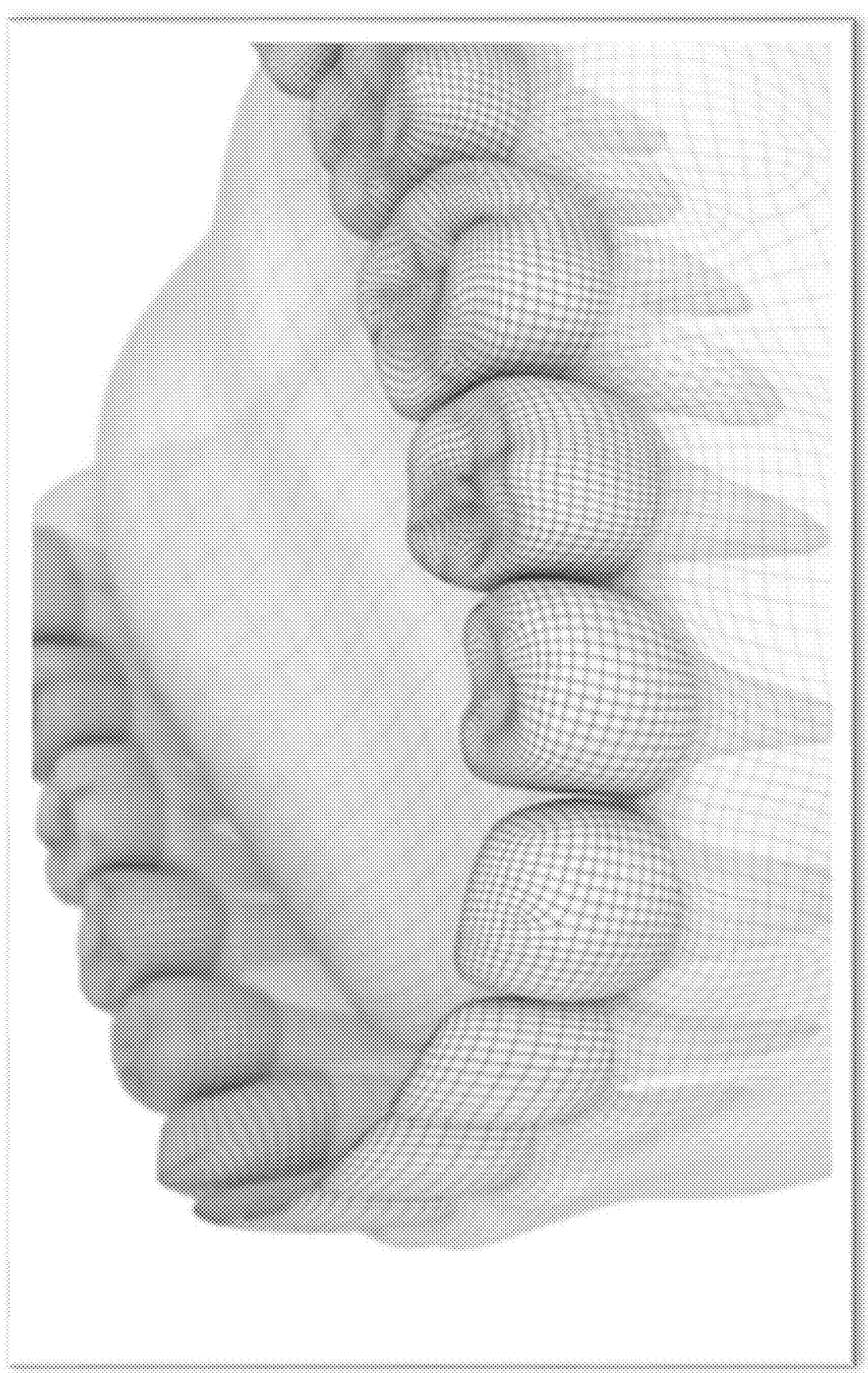
FIG. 13 shows a diagram of a virtual mathematical model of the jaw.

FIG. 13 shows a diagram of a virtual mathematical model of the jaw. This model visualizes hard and soft tissues of the dental system. The practitioner can see detailed images from different angles. The jaw model is combined from models of the teeth, jaw bones, and other virtual mathematical models of anatomical structures of the dental system. The user can switch among these and analyze them separately or together. The mathematical model of the jaw shows the shape and size of all teeth, the dental arch, spatial relationship of anatomical structures of the dental system to each other, and can calculate the measurements (linear and volumetric) of the elements, and can produce the spatial relationships of all the tissues and elements.

Figure 14:
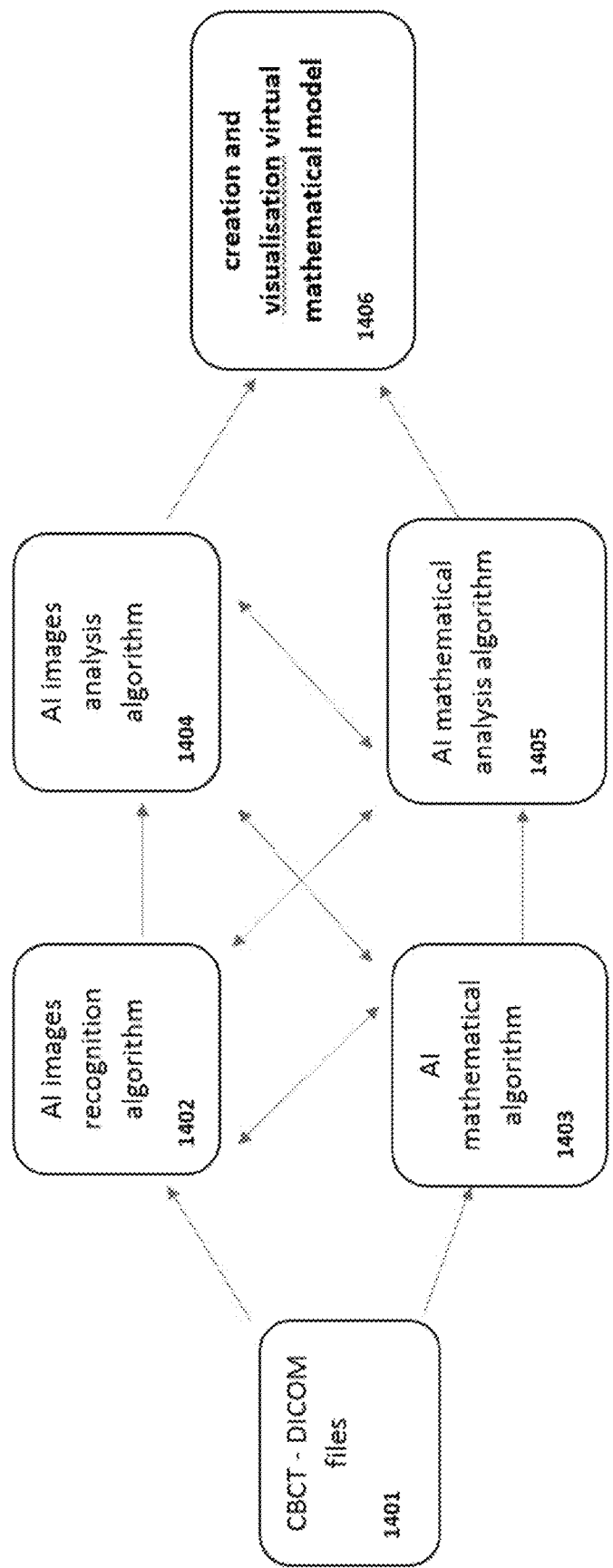
FIG. 14 shows a system diagram of a computer based system that implements the invention.

FIG. 14 shows a system diagram of a computer based system that implements the process of the invention. In block 1401, the image of the dental system, generated using ultrasound PET CT is received. The image, normally in DICOM format, is identified by the AI (block 142), and a mathematical analysis to identify the voxels is performed in block 1403. As a result of 1402 and 1403, the AI identifies the virtual tissues of the dental system, and permits their mathematical analysis by using the voxel as a unit of measurement. Then, the virtual tissues are combined into virtual organs, and then the entire dental system, in block 1404. In parallel, the generation of a coordinate system that permits measurements of all the elements of the dental system is performed in block 1405. These processes are generally related to each other, and performed using a neural network. In block 1406, the visualization of the virtual mathematical model of the dental system is performed.

Having thus described a preferred embodiment, it should be apparent to those skilled in the art that certain advantages of the described method and apparatus have been achieved.

It should also be appreciated that various modifications, adaptations, and alternative embodiments thereof may be made within the scope and spirit of the present invention. The invention is further defined by the following claims.

References (all Incorporated by Reference Herein in their Entirety)
1. voxeltalk.wordpress.com/2016/11/02/dicom-standard/
2. voxeltalk.files.wordpress.com/2016/11/en-iso-12052-2006.pdf 3. voxeltalk.files.wordpress.com/2016/11/dicom-ps3-3-2016d-information-object-definitions.pdf
4. dicom.nema.org/dicom/geninfo/Brochure.pdf
5. www.dicomstandard.org/
6. William C. Scarfe, Christos Angelopoulos. Maxillofacial cone beam computed tomography principles, techniques and clinical applications Springer, Cham 2018, 1242. https://doi.org/10.1007/978-3-319-62061-9
7. Arai Y, Tammisalo E, Iwai K, Hashimoto K, Shinoda K (1999) Development of a compact computed tomographic apparatus for dental use. Dentomaxillofac Radiol 28:245-248
8. Aziz O, Lo B, Pansiot J, Atallah L, Yang G Z, Darzi A (2008) From computers to ubiquitous computing by 2010: health care. Philos Trans A Math Phys Eng Sci 366(1881):3805-3811
9. Cormack A M (1980) Early two-dimensional reconstruction (CT scanning) and recent topics stemming from it. Nobel lecture, Dec. 8, 1979. J Comput Assist Tomogr 4:658-664
10. Fahrig R, Fox A J, Lownie S, Holdsworth D W (1997) Use of a C-arm system to generate true three-dimensional computed rotational angiograms: preliminary in vitro and in vivo results. AJNR Am J Neuroradiol 18:1507-1514
11. Farman A G, Scarfe W C, Hilgers M J, Bida O, Moshiri M, Sukovic P (2005) Dentomaxillofacial cone-beam CT for orthodontic assessment. Int Congress Ser 1281:1187-1190
12. Farman A G, Levato C M, Scarfe W C (2007a) 3D X-ray: an update. Inside Dent 3:70-74
13. Farman A G, Levato C M, Scarfe W C (2007b) A primer on cone beam computed tomography. Inside Dent 3:90-92
14. Feldkamp L A, Davis L C, Kress J W (1984) Practical cone-beam algorithm. J Opt Soc Am A 1:612-619
15. Grangeat P (1991) Mathematical framework of cone beam 3D reconstruction via the first derivate of the radon transform. In: Herman G T, Luis A K A K, Natterer F (eds) Mathematical methods in tomography. Springer, Berlin, pp 66-97
16. Hashimoto K, Arai Y, Iwai K, Araki M, Kawashima S, Terakado M (2003) A comparison of a new limited cone beam computed tomography machine for dental use with a multidetector row helical CT machine. Oral Surg Oral Med Oral Pathol Oral Radiol Endod 95:371-377
17. Calhoun P S, Kuszyk B S, Heath D G, Carley J C, Fishman E K (1999) Three-dimensional volume rendering of spiral CT data: theory and method. Radiographics 19:745-764
18. Cline H E, Lorensen W E, Ludke S, Crawford C R, Teeter B C (1988) Two algorithms for the three-dimensional reconstruction of tomograms. Med Phys 15:320-327
19. Cody D D (2002) AAPM/RSNA physics tutorial for residents: topics in CT. Image processing in CT. Radiographics 22:1255-1268
20. Heidrich W, McCool M, Stevens J (1995) Interactive maximum projection volume rendering. IEEE Proceedings Visualization '95, pp 11-18
21. Kuszyk B S, Heath D G, Bliss D F, Fishman E K (1996) Skeletal 3-D CT: advantages of volume rendering over surface rendering. Skelet Radiol 25:207-214
22. Lorensen W E, Cline H E (1987) Marching cubes: a high resolution 3D surface construction algorithm. Comput Graph 21:163-169
23. Scarfe, W. C., & Angelopoulos, C. (2018). Maxillofacial Cone Beam Computed Tomography.

What is claimed is:

1. A method for forming a virtual 3D mathematical model of a dental system, comprising:
receiving DICOM files representing the dental system;
identifying number and location of voxels of tissues of the dental system;
combining the voxels of the tissues into voxels of organs of the dental system;
combining the organs into the virtual 3D mathematical model of the dental system that includes a full anatomical internal structure of all the organs,
wherein the virtual 3D mathematical models supports linear, non-linear and volumetric measurements of the dental system; and
presenting the virtual 3D mathematical model to a user.

2. The method of claim 1, wherein the DICOM files are based on any of cone beam or multispiral computed tomography, MRT, PET and ultrasonography.

3. The method of claim 1, wherein the tissues include enamel, dentin, pulp, cartilage, periodontium, and jaw bone.

4. The method of claim 3, wherein the organs include teeth, gums, temporomandibular joint and jaw.

5. The method of claim 1, wherein a size of the voxels is between 40 µm and 200 µm.

6. The method of claim 1, wherein the virtual 3D mathematical model includes presence or absence of teeth, shape of the teeth, number of roots in the teeth, root canals in the teeth, pulp stones in the teeth, nodular masses in the pulp of the teeth, calcified masses in the pulp of the teeth, dental fillings, restorative objects, dentures, dental posts, parapulpal pins, dental filling materials, quality of root canal fillings, dental bone implants, and prosthetic dentures supported by implants.

7. The method of claim 1, wherein the virtual 3D mathematical model includes linear dimensions of teeth and parts of teeth in sagittal, frontal, and transversal planes, length of root canals, shapes and diameters of the root canals, areas of occlusal surface and contacts, areas of points of contact, volumetric dimensions of defects in hard tissues of teeth and jawbones, and volumetric dimensions of restorations.

8. The method of claim 1, wherein the virtual 3D mathematical model compares an initial state of the dental system to a later state of the dental system.

9. The method of claim 1, wherein the virtual 3D mathematical model shows dynamical aging of the dental system over time.

10. The method of claim 1, wherein the virtual 3D mathematical model calculates biomechanics of individual elements of the dental system or the system as a whole.

11. The method of claim 1, wherein the virtual 3D mathematical model's temporomandibular joint movement data using axiography to replicate a virtual natural movement of a lower jaw.

12. The method of claim 1, wherein the virtual 3D mathematical model sets up a coordinate grid used to calculate location and volumetric parameters of dental treatment.

13. A system for forming a virtual 3D mathematical model of a dental system, comprising:
a processor and a memory coupled to the processor;
a plurality of DICOM files representing the dental system;
the dental system being divided into a plurality of voxels, the voxels identified by number and location of voxels based on tissues to which they belong;
the voxels of the tissues combined by the processor into organs of the dental system;

the voxels of the organs combined into the virtual 3D mathematical model of the dental system that includes a full anatomical internal structure of all the organs by the processor, wherein the virtual 3D mathematical models supports linear, non-linear and volumetric measurements of the dental system; and a display showing the virtual 3D mathematical model to a user.

14. A non-transitory, computer-readable medium containing instructions for forming a virtual 3D mathematical model of a dental system that, when executed by a hardware-based processor, performs:

receiving DICOM files representing the dental system;

identifying number and location of voxels of tissues of the dental system;

combining the voxels of the tissues into voxels of organs of the dental system;

combining the organs into the virtual 3D mathematical model of the dental system that includes a full anatomical internal structure of all the organs, wherein the virtual 3D mathematical models supports linear, non-linear and volumetric measurements of the dental system; and presenting the virtual 3D mathematical model to a user.

* * * * *